US010330593B1

(12) United States Patent
Dobler et al.

(10) Patent No.: US 10,330,593 B1
(45) Date of Patent: Jun. 25, 2019

(54) REAL TIME SPATIAL MAPPING OF ATMOSPHERIC GAS DISTRIBUTIONS

(71) Applicants: Eagle Technology, LLC, Melbourne, FL (US); Atmospheric and Environmental Research, Inc., Lexington, MA (US)

(72) Inventors: Jeremy T. Dobler, Roanoke, IN (US); T. Scott Zaccheo, Arlington, MA (US); Michael G. Braun, Fort Wayne, IN (US); Nathan J. Blume, Churubusco, IN (US); Timothy G. Pernini, Chelmsford, MA (US)

(73) Assignees: Eagle Technology, LLC, Melbourne, FL (US); Atmospheric and Environmental Research, Inc., Lexington, MA (US)

( * ) Notice: Subject to any disclaimer, the term of this patent is extended or adjusted under 35 U.S.C. 154(b) by 0 days.

(21) Appl. No.: 16/042,539

(22) Filed: Jul. 23, 2018

(51) Int. Cl.
*G01N 21/31* (2006.01)
*G01N 21/39* (2006.01)

(52) U.S. Cl.
CPC ......... *G01N 21/39* (2013.01); *G01N 21/3103* (2013.01); *G01N 2201/126* (2013.01); *G01N 2201/12723* (2013.01)

(58) Field of Classification Search
CPC ............... G01N 21/39; G01N 21/3103; G01N 2201/126; G01N 2201/12723
USPC ................................ 356/437, 436, 432, 326
See application file for complete search history.

(56) References Cited

U.S. PATENT DOCUMENTS

| 5,339,330 | A | * | 8/1994 | Mallinckrodt | ..... H04B 7/18532 370/320 |
| 5,343,043 | A | * | 8/1994 | Johnson | ............ G01N 21/3504 250/338.5 |
| 5,650,845 | A | * | 7/1997 | Kebabian | ........... G01N 21/3103 250/339.13 |
| 8,294,899 | B2 | | 10/2012 | Wong | |
| 8,781,755 | B2 | | 7/2014 | Wong | |
| 9,599,529 | B1 | | 3/2017 | Steele et al. | |
| 9,696,245 | B1 | | 7/2017 | Rella | |
| 2003/0026532 | A1 | * | 2/2003 | Murry | ....................... G01J 9/00 385/27 |
| 2005/0078957 | A1 | * | 4/2005 | Hendow | ................... G01J 3/36 398/33 |
| 2011/0313635 | A1 | * | 12/2011 | Blanc | .................. F02D 41/1451 701/102 |
| 2014/0168649 | A1 | * | 6/2014 | Smith | ................... G01J 3/0291 356/409 |

(Continued)

*Primary Examiner* — Isiaka O Akanbi
(74) *Attorney, Agent, or Firm* — Edell, Shapiro & Finnan, LLC

(57) ABSTRACT

An apparatus is provided that includes a plurality of reflectors arranged over an area, and a plurality of transceivers. A first of the transceivers is configured to transmit radiation at each of the plurality of reflectors at a first wavelength and a second wavelength, and receive radiation reflected from each of the plurality of reflectors. A second of the plurality of transceivers is configured to transmit radiation at each of the plurality of reflectors at a third wavelength and a fourth wavelength and receive radiation reflected from each of the plurality of reflectors. The apparatus includes a processor configured to calculate a change in concentration of a gas within the area between a first time and a second time based upon signals received from the transceivers.

20 Claims, 15 Drawing Sheets

(56) References Cited

U.S. PATENT DOCUMENTS

| | | | |
|---|---|---|---|
| 2014/0204382 A1* | 7/2014 | Christensen | G01N 21/39 356/402 |
| 2015/0268159 A1* | 9/2015 | Tabaru | G01N 21/39 356/437 |
| 2016/0011101 A1* | 1/2016 | Ognibene | G01N 21/3103 356/437 |

* cited by examiner

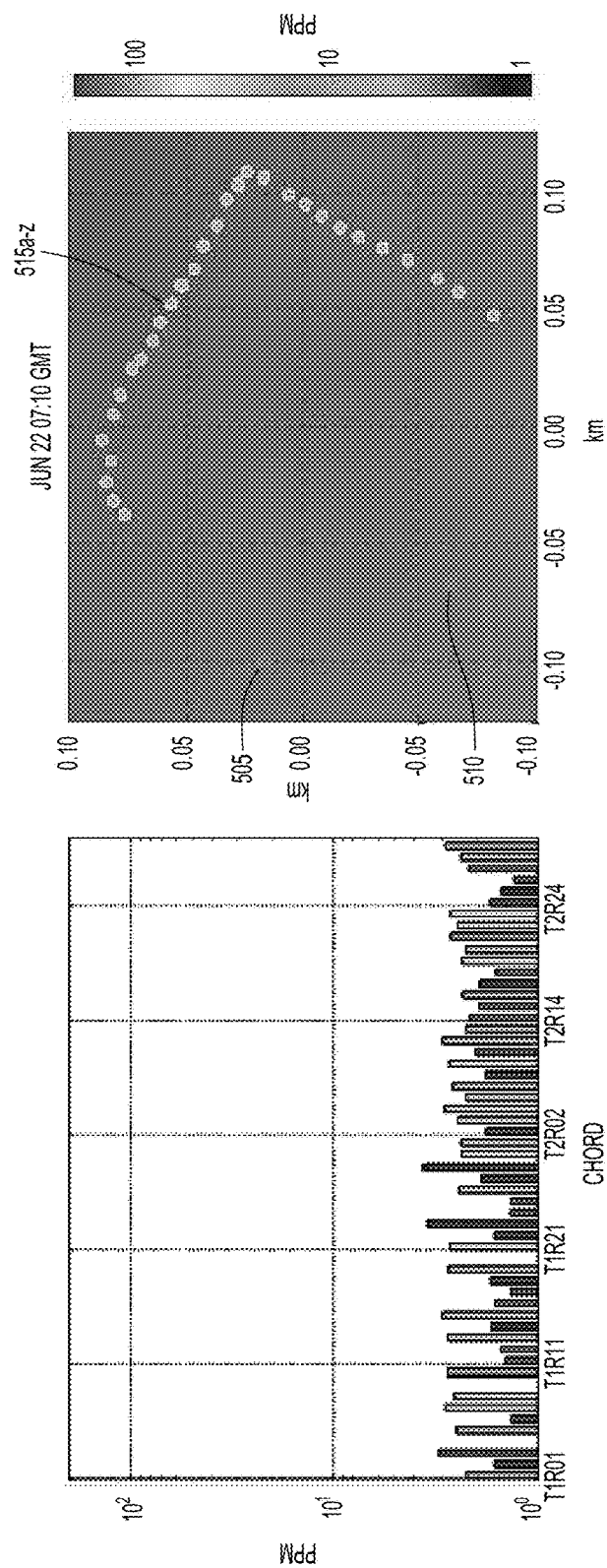

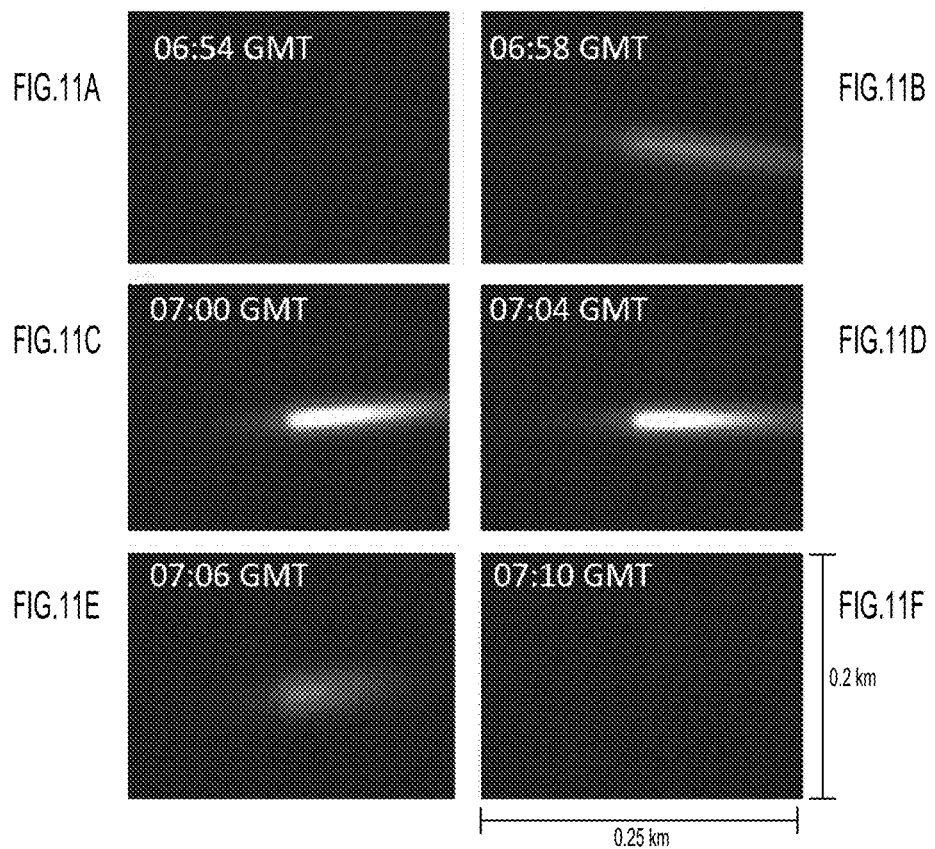
FIG.11A 06:54 GMT
FIG.11B 06:58 GMT
FIG.11C 07:00 GMT
FIG.11D 07:04 GMT
FIG.11E 07:06 GMT
FIG.11F 07:10 GMT
0.2 km
0.25 km
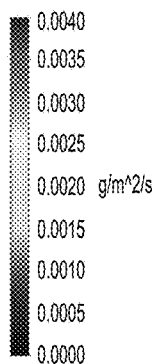
0.0040
0.0035
0.0030
0.0025
0.0020 g/m^2/s
0.0015
0.0010
0.0005
0.0000

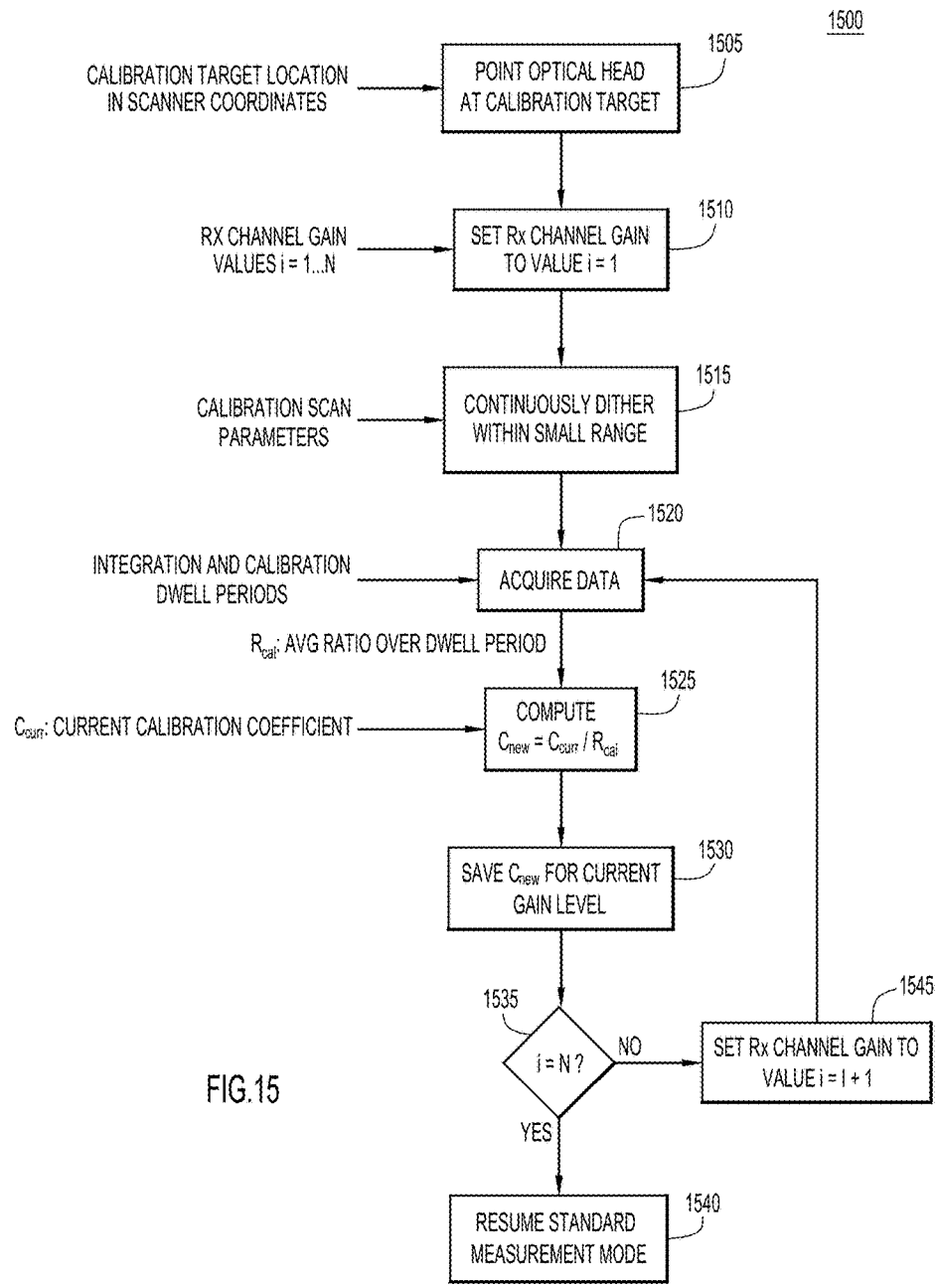

REAL TIME SPATIAL MAPPING OF ATMOSPHERIC GAS DISTRIBUTIONS

TECHNICAL FIELD

The present disclosure relates to the sensing and detection of atmospheric gas concentrations.

BACKGROUND

Related art approaches for mapping atmospheric gas concentrations use point measurement devices or ground chamber units that are labor intensive and only provide limited spatial or temporal resolution. These systems also provide little feedback to site operators, and their outputs are received by users with a significant delay from the time at which measurements were taken due to collection times or quality control of the data. For example, individual users may be required to place such point sensors and return to the sensors to retrieve the data at a later time.

Infrared cameras are dynamic, mature solutions for measuring atmospheric gas distributions and are currently used in the Oil and Gas industry. Yet, these infrared cameras lack sensitivity, can cover only limited ranges, and are susceptible to environmental factors, such as background temperature variations.

BRIEF DESCRIPTION OF THE DRAWINGS

FIG. 10A is a sixth graph of measurement path concentrations for use in real-time spatial mapping of atmospheric gas distribution, according to an example embodiment.

FIG. 10B is a sixth real-time spatial map of atmospheric gas distributions generated from the measurement paths graphed in FIG. 10A, according to an example embodiment.

FIGS. 11A-F are spatial maps of gas emissions calculated from the measurements and spatial concentration maps illustrated in FIGS. 5A-10A and 5B-10B, respectively, according to an example embodiment.

FIG. 15 is a process flow for a calibration process for transceivers configured to provide real-time spatial mapping of atmospheric gas distribution, according to an example embodiment.

DESCRIPTION OF EXAMPLE EMBODIMENTS

Overview

Figure 1:
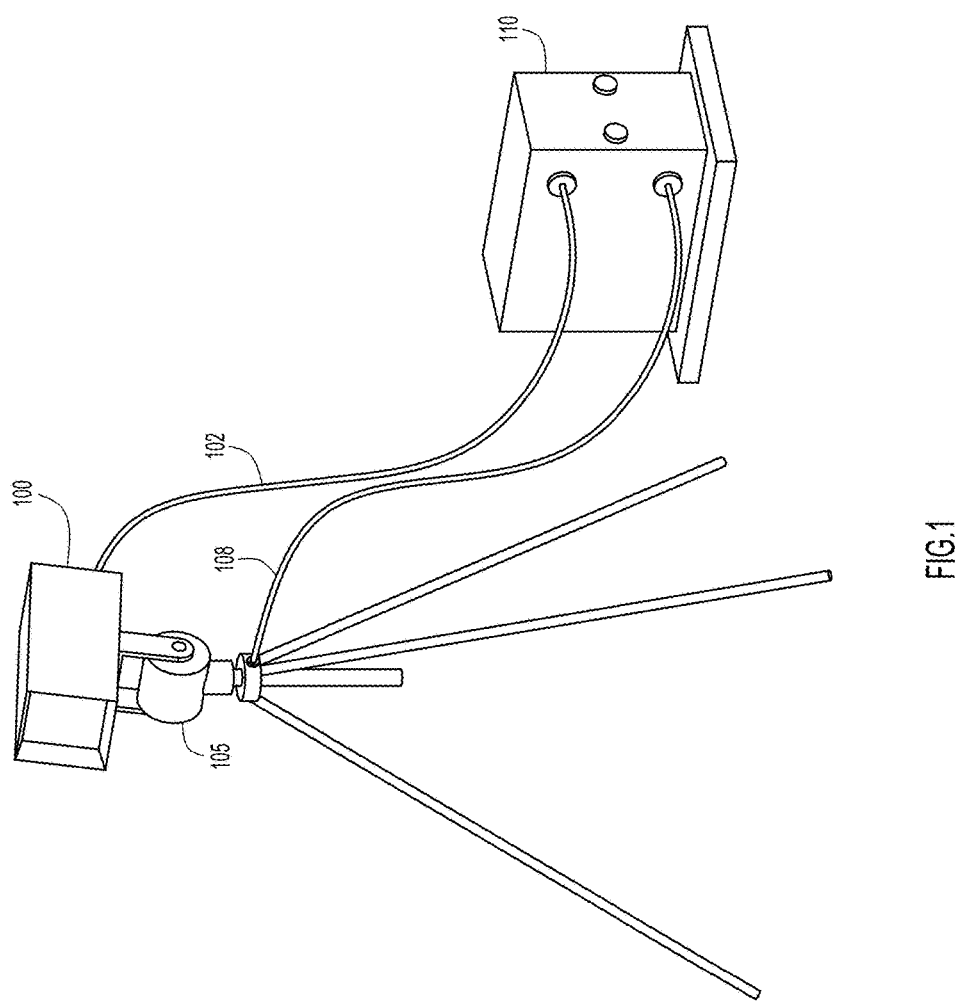
FIG. 1 is an illustration of a transceiver configured to provide real-time spatial mapping of atmospheric gas distribution, according to an example embodiment.

An apparatus is provided that includes a plurality of reflectors arranged over an area, and a plurality of transceivers. A first of the transceivers is configured to transmit radiation at each of the plurality of reflectors at a first wavelength and a second wavelength, receive radiation reflected from each of the plurality of reflectors at the first wavelength and the second wavelength, and generate first signals indicative of intensities of the radiation received at the first wavelength and the second wavelength from each of the plurality of reflectors. A second of the plurality of transceivers is configured to transmit radiation at each of the plurality of reflectors at a third wavelength and a fourth wavelength, receive radiation reflected from each of the plurality of reflectors at the third wavelength and the fourth wavelength, and generate second signals indicative of intensities of the radiation received at the third wavelength and the fourth wavelength from each of the plurality of reflectors. The apparatus includes a processor configured to receive the first signals and the second signals; calculate a first concentration of a gas within the area based upon the first signals and the second signals received at a first time; calculate a second concentration of the gas within the area based upon the first signals and the second signals received at a second time; and calculate a change in concentration of the gas within the area between the first time and the second time.

According to other example embodiments, a method is provided that includes transmitting, from a first transceiver, radiation at a first wavelength and a second wavelength to each of a plurality of reflectors, wherein the plurality of reflectors are arranged within an area. The method further includes transmitting, from a second transceiver, radiation at a third wavelength and a fourth wavelength to each of a plurality of reflectors. Radiation reflected from each of the plurality of reflectors at the first wavelength and the second wavelength is received at the first transceiver and radiation reflected from each of the plurality of reflectors at the third wavelength and the fourth wavelength is received at the second transceiver. An intensity of the radiation reflected from each of the plurality of reflectors at the first wavelength and the second wavelength at a first time and a second time is determined, as is an intensity of the radiation reflected from each of the plurality of reflectors at the third wavelength and the fourth wavelength. A first concentration of a gas within the area is calculated based upon the intensity of the radiation reflected from each of the plurality of reflectors at the first wavelength and the second wavelength at the first time and the intensity of the radiation reflected from each of the plurality of reflectors at the third wavelength and the fourth wavelength at the first time. A second concentration of the gas within the area is calculated based upon the intensity of the radiation reflected from each of the plurality of reflectors at the first wavelength and the second wavelength at the second time and the intensity of the radiation reflected from each of the plurality of reflectors at the third wavelength and the fourth wavelength at the second time. A change in concentration of the gas within the area between the first time and the second time is calculated.

EXAMPLE EMBODIMENTS

Described herein are techniques for utilizing an Integrated Laser Absorption Spectroscopy system for real-time spatial mapping of atmospheric gas distributions. According to specific example embodiments, a real-time autonomous measurement system may monitor one or more gases, such as carbon dioxide and methane, over large areas, up to and including areas on the order of 25 $km^2$. The described embodiments may provide for continuous monitoring of, for example, ground carbon storage facilities, urban environments, and oil and gas facilities. The techniques of the present disclosure arrange reflectors over an area of interest. Specific example embodiments of such arrangements are illustrated in FIGS. 2, 13, 14A, and 14B (described in greater detail below). Transceivers (described in greater detail with reference to FIG. 1 below) are used to project on- and off-line radiation at the reflectors. Based upon the signals received back from the reflectors, gas concentrations throughout the area of interest may be determined via processing as illustrated in FIGS. 3, 4, 8, and 11 (described in greater detail below). The processing may include a web-based real-time analysis and dissemination tool set. This tool set may further provide two-dimensional maps of an estimated spatial distribution of the measured gas concentration. According to specific example embodiments, intensity-modulated, continuous-wave (IMCW) laser transceivers may be used in conjunction with the reflectors. Also described herein are techniques to estimate the emission or flux of the measured gases using the concentration maps of the measured gases. The techniques may also include self-calibration methods to correct for instrumental drift.

With reference now made to FIG. 1, depicted therein is an example transceiver 100 according to the techniques described herein. Transceiver 100 is mounted to a mount 105 which allows transceiver 100 to be directed at a plurality of locations. Other example embodiments may use other techniques, such as optical beam steering techniques, to selectively direct the transceiver at a plurality of locations. As will be described in more detail below, transceiver 100 will be directed towards a plurality of reflectors, either via mount 105 or through other techniques. Transceiver 100 is optically and/or electrically connected to processing and communication module 110. As will also be described in more detail below, processing and communication module 110 may control mount 105 to appropriately direct transceiver 100 towards an intended reflector, and processing and communication module 110 may receive signals from transceiver 100 to provide spatial mappings of atmospheric gas distributions. While transceiver 100 and processing and communication module 110 are illustrated as being housed in separate enclosures, transceiver 100 and processing and communication module 110 may be embodied as a single device in, for example, a single enclosure.

Transceiver 100 is configured to both project and receive electromagnetic radiation. According to the techniques of the present disclosure, transceiver 100 is configured to project electromagnetic radiation to reflectors across an area in which atmospheric gas measurements are to be made. The wavelength or frequency of the electromagnetic radiation is determined by the gas being measured. Specifically, transceiver 100 may be configured to project electromagnetic radiation for at least a first wavelength and a second wavelength, such that the first wavelength is absorbed by the gas to be measured (i.e., an on-line wavelength or frequency) and the second wavelength is less absorbed by the gas to be measured (i.e., an off-line wavelength or frequency). The first and second wavelengths may be selected so that other than their gas absorption properties, the first and second wavelengths have similar optical properties over the path from transceiver 100, to the reflector, and from the reflector back to transceiver 100. The first and second wavelengths may also be selected to minimize absorption from gases other than the gas to be measured.

Transceiver 100 may also be configured to perform atmospheric gas distribution measurements for a plurality of different gases. According to such embodiments, transceiver 100 will be configured to project two or more wavelengths for each of the plurality of gases. For example, by utilizing more than two wavelengths or frequencies, the dynamic range of the measurements discussed herein may be improved. According to example embodiments, transceiver 100 may be configured to transmit at four wavelengths: a first wavelength that is absorbed by a first gas but not by a second gas, a second wavelength with less, or no, absorption by any of the plurality of gases but that has similar optical properties to the first wavelength over the path from transceiver 100 to the reflector, a third wavelength that is absorbed by the second gas but not the first gas, and a fourth wavelength not absorbed by any of the plurality of gases but that has similar optical properties to the third wavelength over the path from transceiver 100, to the reflector. For example, to measure concentrations of carbon dioxide, an on-line wavelength of 1571.1129 nm may be used, as this wavelength is absorbed by carbon dioxide. An off-line wavelength of 1571.0529 nm may be used, as this wavelength is less absorbed by carbon dioxide, but will otherwise respond to other aspects (humidity or water vapor, other gases, scattering, etc.) of the environment within the area of interest in a manner optically similar to that of the on-line wavelength, or in a manner separable using standard spectroscopic techniques. For methane, transceiver 100 may be configured to transmit an on-line wavelength of 1650.9580 nm and an off-line wavelength of 1651.0298 nm. If gases other than carbon dioxide or methane are being measured, other wavelengths may be determined to be suitable on-line and off-line wavelengths.

According to other example embodiments, three wavelengths of frequencies may be used: an on-line wavelength or frequency for the first gas, an on-line wavelength of frequency for the second gas, and an off-line frequency used for both of the gases. Still other example embodiments may use multiple on-line wavelengths or frequencies for each gas and/or multiple off-line wavelengths or frequencies for each gas, thereby improving the dynamic range of the measurements. Transmitter 100 may be configured to transmit these wavelengths or frequencies concurrently or separately.

The above described wavelengths or frequencies may also be tailored to specific gas concentrations. For example, with very high concentrations, the on-line wavelength may be altered to be slightly different than the most absorptive wavelength. In other words, the on-line wavelength may be set as "slightly off-line" if the concentration of the gas being measured is known to be of a high enough concentration. In these high concentrations, a reduced absorption sensitivity may be beneficially used to increase the accuracy of the measurements. For example, in areas of high concentration, the absorption of the most absorbed wavelength may be such that it would be difficult to detect differences in absorption of the radiation because all or significant portions of the laser energy at the on-line wavelength would be absorbed before returning to the transceiver. By slightly altering the on- and off-line wavelengths, the overall sensitivity of the measurements may be increased. According to one such example embodiment, the on- and off-line values for a methane measurement may be determined to be 1651.0000 nm and 1651.0700 nm, respectively. These wavelengths may be determined through a process that includes simulating concentration levels assuming a particular configuration and source rates under varying wind conditions, then running the spectroscopy tests to optimize the absorption using a given pair of off- and partially-off-line wavelengths. In a further embodiment, a plurality of wavelengths may be selected, each with differing absorption by the gas to be measured, to enable transceiver 100 to be sensitive over a very wide dynamic range of concentrations.

According to specific example embodiments, transceiver 100, optionally including processing and communication module 110, may be embodied as an IMCW laser absorption spectrometer (LAS). As understood by the skilled artisan, an IMCW LAS is an instrument that measures the differential absorption by a target gas of interest using electromagnetic radiation transmitted simultaneously at two, or more, different wavelengths or frequencies and using unique intensity modulation for each different wavelength to uniquely identify the quantity of electromagnetic radiation transmitted and/or received by transceiver 100. Therefore, an IMCW LAS may be configured to transmit electromagnetic radiation at the on- and off-line wavelengths for the plurality of gases that are to be measured.

An IMCW LAS may utilize lock-in processing or matched filters to separate the individual channels received at a transceiver 100. Lock-in processing employs a homodyne detection scheme and low-pass filtering to measure a signal's amplitude and phase relative to a periodic reference. Accordingly, an IMCW LAS may utilize such processing when the transmitted signal modulation is known. This permits the received signal to be measured with great accuracy even in the presence of significant noise. Furthermore, as will be described below with reference to FIGS. 2, 13, 14A, and 14B, the techniques of the present application may utilize a plurality of transceivers 100. If each transceiver utilizes a different modulation pattern, the transceivers may utilize the same wavelength or frequencies while utilizing lock-in processing techniques to prevent cross-talk between the radiation transmitted by each of the transceivers.

Utilizing lock-in processing also permits a single transceiver 100 to simultaneously transmit a plurality of similar wavelengths or frequencies, but still distinguish the received signals in the electrical domain. More specifically, if the signals of similar wavelength are transmitted simultaneously, but with different modulation patterns, the signals may be distinguished in the electrical domain using lock-in processing techniques. Absent this processing, attempting to distinguish the received signals in the optical domain may be difficult or impossible to achieve with a necessary or desired level of accuracy.

The description above refers to intensity modulated modulation patterns for the radiation transmitted by the transceiver 100. According to other example embodiments, the modulation provided by the transceiver may be frequency modulation.

Because the IMCW method allows the on- and off-line wavelengths to be transmitted simultaneously, and both beams have similar optical properties over the transmission paths, both beams will experience the same disturbances in the modulation waveform (i.e., "noise"). The noise common to the two wavelengths will cancel out when the measurements are compared, allowing the differential transmission to be measured with a high degree of accuracy even in the presence of significant atmospheric noise.

Transceiver 100 may also be configured with optoelectronic elements to convert the received electromagnetic radiation from optical signals into electrical signals. Transceiver 100 may be configured with, for example, photodiodes or charge coupled device (CCD) cameras. Such devices convert the electromagnetic radiation from an optical value to an electrical one that may be sent to processing and communication module 110. Such electrical signals may be sent to processing and communication module 110 via, for example, electrical cables contained in transceiver communication link 102. According to other example embodiments, transceiver 100 receives optical signals and communicates them to processing and communication module 110 through optical means. For example, an optical wave guide, such as an optical fiber, may communicate the optical signals to processing and communication module 110 through transceiver communication link 102. Processing and communication module 110 may be configured with optoelectronic elements to convert these received optical signals into electrical signals.

In order to direct transceiver 100 at each of the plurality of reflectors, as will be described in greater detail below, transceiver 100 is mounted to mount 105. Mount 105 is configured to rotate to direct transceiver 100 towards each of the plurality of reflectors. Mount 105 may be configured to direct transceiver 100 with one or more degrees of freedom. For example, mount 105 may be configured with a pan/tilt positioner configured to rotate through an azimuthal angle (i.e., a horizontal rotation). Mount 105 may also be configured to rotate through an elevation angle (i.e., a vertical rotation). These two degrees of freedom permit accurate positioning of the transceivers 100. The two degrees of freedom also allow for measurement of other than horizontal two-dimensional areas of interest. Furthermore, the two degrees of freedom also permit three dimensional volumes of interest to be evaluated. In other words, the techniques of the present disclosure are not limited to horizontal two-dimensional areas of interest. Through appropriate positioning of reflectors, the techniques of the present disclosure may be applied to any orientation of two-dimensional areas of interest or three-dimensional volumes of interest. Similar positioning of transceiver 100 may be achieved through other means, including optical beam steering techniques.

Mount 105 may be configured with actuators to automatically position transceiver 100 to direct electromagnetic radiation at each of the reflectors. More specifically, processing and communication module 110 may be configured to send signals to mount 105 through mount communication link 108 to position transceiver 100 to direct electromagnetic radiation towards a reflector. According to specific example embodiments, processing and communication module 110 may send signals to mount 105 to position transceiver 100 such that it is generally directed towards a reflector and send signals to transceiver 100 to transmit electromagnetic radiation towards the reflector. This electromagnetic radiation will be reflected from the reflector and received at transceiver 100. Transceiver 100 may communicate these signals to processing and communication module 110 through transceiver communications link 102, in response to which processing and communication module 110 may send additional signals to mount 105 through mount communication link 108 to refine the position of transceiver 100. This process may continue until an intensity of reflected radiation received at transceiver 100 is determined to be at a maximum or determined to be greater than a threshold value. Optical beam steering techniques may implement similar feedback techniques to aim and position transceiver 100.

Processing and communication module 110 may be configured to provide specific transmission parameters for each reflector to which transmitter 100 directs radiation. In other words, processing and communication module 110 may provide reflector-specific parameters based upon the nature of the path between the transmitter 100 and the reflector. These path- or reflector-specific settings may allow a much wider range of path lengths to be accommodated at a fixed laser power, thereby increasing flexibility in site configuration and the ability to adapt to irregular site shapes and sizes. Depending on the length of a particular path between transmitter 100 and the reflector, the wavelengths or frequencies of the measurement radiation and the transmission power may be optimized. For example, selecting an on-line wavelength or frequency that will be more highly absorbed may be beneficial for a shorter path between transceiver 100 and a reflector. Along such a shorter measurement path, using a higher absorption frequency may result in a greater difference between the on-line and off-line received signals, providing a more accurate determination of the gas concentration throughout the measured path. On the other hand, for longer paths, an on-line wavelength or frequency that exhibits a lower absorption by the gas being measured may be beneficial to ensure that a sufficiently strong signal is received back at the transceiver. Additionally, optical or electrical gain of the receiver components (photodetector, transimpedance amplifier, etc.) may be optimized on a path-by-path basis. Similarly, integration times may be tailored on a per-path basis. In fact, any calibration value associated with a given gain setting may also be adjusted on a path-by-path basis. Furthermore, as noted above, the wavelength or frequency of the transmitted radiation may be tailored based upon the concentration of the gas within the path between the transceiver 100 and the reflector. Similarly, the wavelength or frequency of the transmitted radiation may be tailored to specific weather or atmospheric conditions. Accordingly, processing and communication module 110 may alter the transmitter parameters, including the wavelength or frequency of the transmitted radiation, such that the transmitted wavelength or frequency changes between measurements, even for the same path if other parameters, like the weather, change. Accordingly, the measurement parameters, including the on-line and off-line wavelengths or frequencies, may be time-dependent.

Processing and communication module 110 may be configured with a wireless or wired communication unit, such as a cellular transceiver or a network interface unit, that allows processing and communication module 110 to send signals to, for example, a cloud processing system, as discussed in greater detail below with reference to FIG. 12. Processing and communication module 110 may also be configured to receive data, such as real-time weather and wind data, that may be incorporated into the real-time spatial mapping of atmospheric gas distributions techniques described herein. Processing and communication module 110 may also include memory or storage devices, including magnetic hard disks, solid state drives, and/or removable media drives (e.g., floppy disk drive, optical disc drives, removable magneto-optical drives, and optical storage drives). One or more of these drives may be used to store data received from transceiver 100 so that the data may be utilized for the real-time spatial mapping of atmospheric gas distributions techniques described herein.

Through the use of processing and communication module 110, the techniques of the present disclosure may provide spatial mappings of atmospheric gas concentrations and gas flux in real-time and in a continuous manner. Related art techniques for determining atmospheric gas concentrations generally rely on user-positioned point sensors. Users must position these sensors in a plurality of locations, allow the sensors to take measurements, each at a single location, and then employ complex modeling to extrapolate the single point measurements, often requiring that specific wind conditions be met. To determine atmospheric concentrations over a wide geographical region, the user must locate a significant quantity of sensors throughout the area of interest and employ increasingly complex modeling techniques. In contrast, the communication and control features provided by processing and communication module 110, and the long-range measurement functions of transceivers 100, allow for the continuous and real-time generation of concentration and flux mappings of large spatial regions. Specifically, processing and communication module 110 is configured to control transceivers 100 to take multiple measurements, continuously, without requiring a user to physically access either transceiver 100 or processing and communication module 110. Similarly, the processing and communication features of processing and communication module 110 allow for the measurements acquired by transceivers 100 to be provided to users in real-time, as will be discussed in more detail with reference to FIG. 12, below.

Figure 2:
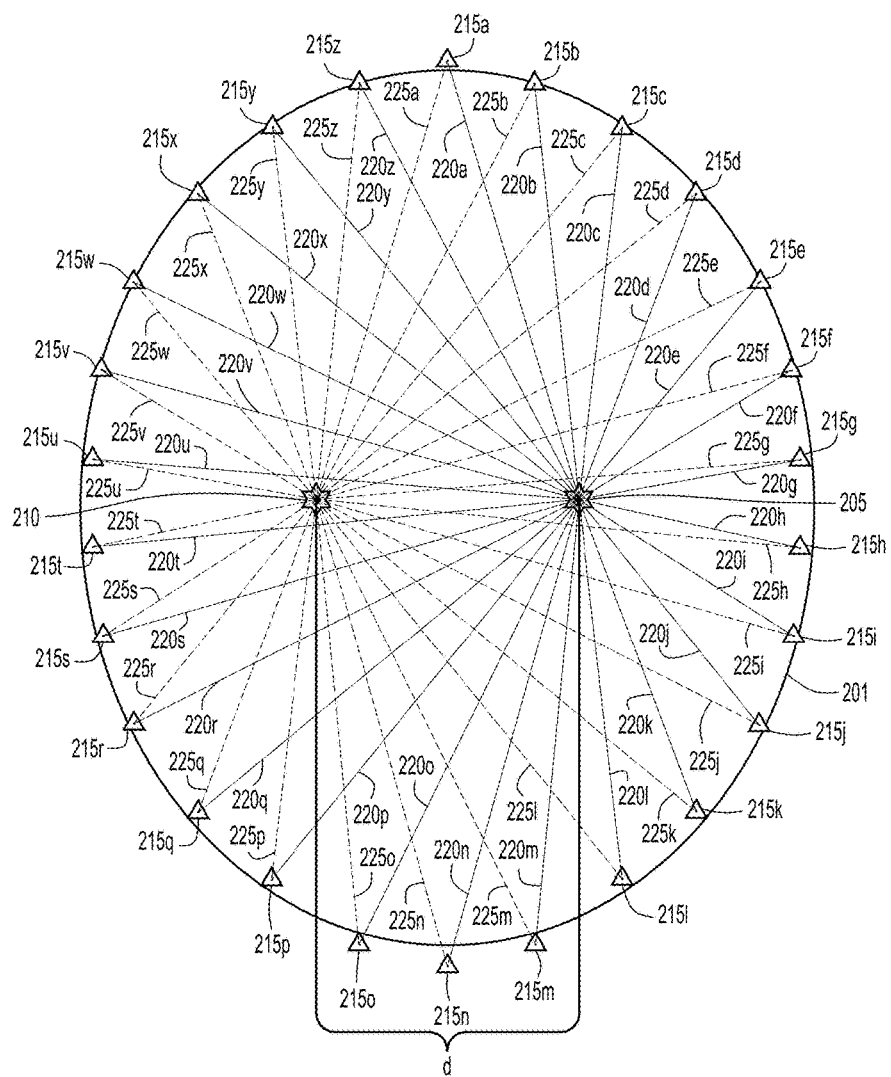
FIG. 2 is a first arrangement of transceivers and reflectors configured to provide real-time spatial mapping of atmospheric gas distribution, according to an example embodiment.

With reference now made to FIG. 2, depicted therein is a first example arrangement of transceivers and reflectors configured to carry out the real-time spatial mapping of atmospheric gas distributions of the present disclosures for area of interest 201. As illustrated in FIG. 2, transceivers 205 and 210 are arranged within an elliptical arrangement of reflectors 215a-z. Such an elliptical arrangement of reflectors 215a-z may be utilized so that a minimum or smaller number of reflectors is used to measure area of interest 201.

Each of transceivers 205 and 210 project electromagnetic radiation at each of reflectors 215*a-z* over a plurality of paths or "chords," according to the terminology used herein. The chords over which transceiver 205 transmits and receives electromagnetic radiation are illustrated through solid lines 220*a-z*, and the chords over which transceiver 210 transmits and receives electromagnetic radiation are illustrated through dashed lines 225*a-z*. Because both transceivers 205 and 210 utilize each of reflectors 215*a-z*, area of interest 201 is measured with a relatively small number of reflectors 215*a-z*. The arrangement of reflectors 215*a-z* and transceivers 205 and 210 may also increase or maximize area of interest 201 with just two transceivers. By combining the measurement values received from each of chords 220*a-z* and 225*a-z*, a map of the gas concentration throughout area of interest 201 may be determined, as will be described in greater detail below with reference to FIGS. 3 and 4.

As illustrated, the distance "d" between transceivers 205 and 210 results in chords 220*a-z* providing different paths through area of interest 201 than those provided by chords 225*a-z*. These different or diverse paths facilitate the operations used to generate the real-time spatial mapping of atmospheric gas distributions of the present disclosures. Additionally, because the arrangement of transceivers 205 and 210 and reflectors 215*a-z* is such that each of transceivers 205 and 210 transmits and receives over the entire area of interest 210 by transmitting to and receiving from each of reflectors 215*a-z*, an arrangement like that illustrated in FIG. 2 is configured to provide a large coverage area with a relatively small number of reflectors 215*a-z*.

While FIG. 2 illustrates an example embodiment in which two transceivers 205 and 210 are utilized in order to benefit from the additional chords or paths provided by the two transceivers, and to also benefit from the diverse paths provided by the two transceivers 205 and 210, the techniques of the present application are not limited to embodiments that include a plurality of transceivers. Accordingly, the techniques of the present application may also be applied to embodiments in which a single transceiver is employed to transmit and receive radiation from each of the plurality of reflectors. The single transceiver may be configured to transmit and receive at a plurality of wavelengths such that the single transceiver may make measurements for a plurality of gases.

As noted above, when two or more transceivers 205 and 210 are utilized, the two transceivers 205 and 210 may use different on-line and/or off-line wavelengths or frequencies when making measurements over chords 225*a-z* and 220*a-z*, respectively. The use of the different wavelengths or frequencies may be done to provide a better dynamic range, to facilitate the different lengths of chords 220*a-z* and 225*a-z*, and to avoid cross-talk between the transceivers 205 and 210. Similarly, the modulation of the signals sent by transceivers 205 and 210 may be different between the two transceivers to avoid cross-talk between transceivers 205 and 210.

Once electromagnetic radiation with the on-line and off-line wavelengths is projected to each of reflectors 215*a-z*, the received intensity values are sent from the transceivers 205 and 210 to a processing and communication module, like processing and communication module 110 of FIG. 1. Also included in this data may be an indication of the intensity with which the radiation was transmitted from transceivers 205 and 210 towards each of the reflectors 215*a-z*. These transmitted intensities may be used as a reference value against which the intensity values of the radiation reflected from reflectors 215*a-z* will be compared.

Once received at the processing and communication module, the received data may be used to generate the real-time spatial mapping of atmospheric gas distributions of the present disclosures. The processing and communication module may also communicate the received data over a wired or wireless channel to a cloud-based or otherwise remote backend system for the generation of the real-time spatial mapping of atmospheric gas distributions of the present disclosures.

According to additional example embodiments, transceivers 205 and 210 may be configured to carry out ranging operations. For example, once the transceivers 205 and 210 are positioned relative to reflectors 215*a-z*, the distance between the transceivers and reflectors may be determined. Specifically, the transceivers may be configured to determine the phase delay of a reflected signal to determine the distance between the transceiver and one or more reflectors 215*a-z*. Similarly, the distance d between the transceivers may be similarly calculated. Such techniques permit arrangements like that illustrated in FIG. 2 to self-determine their specific layouts.

In addition to ranging operations, by pointing transceivers 205 and 210 at each other, the relative measurements of the two transceivers may be normalized. For example, a reflector may be arranged on or near transceivers 205 and 210 so that the two transceivers may measure the same column of air. Specifically, transceiver 205 may be pointed at the reflector arranged at or near transceiver 210, and transceiver 210 may be pointed at the reflector at or near transceiver 205. The radiation received at the two transceivers, once processed, should result in similar or identical gas concentration measurements because the chords being measured correspond to the same column of air. According to other example embodiments, if the two transceivers utilize the same wavelengths or frequencies, by positioning transceivers 205 and 210 such that the receiver for transceiver 205 receives the electromagnetic radiation transmitted by transceiver 210, and vice versa, transceivers 205 and 210 can simultaneously measure the same column of air. Accordingly, comparing the measurements from the two transceivers pointed at each other allows for assessment of bias, which can be used along with short-path calibration to provide 2-point calibration for increased calibration accuracy.

While reflectors 215*a-z* may be embodied as any surface that reflects/scatters light back to the transceivers 205 and 210, reflectors 215*a-z* may be beneficially embodied as retroreflectors. Retroreflectors are optical devices configured to reflect electromagnetic radiation along a path parallel to the path from which the radiation was received so long as the radiation is incident within an appropriate angular range. If correctly aligned, a retroreflector will reflect radiation along the same path from which the radiation was received. Accordingly, transceivers 205 and 210 may be positioned to direct radiation onto reflectors 215*a-z* such that reflectors 215*a-z* reflect the radiation along the same path from which it was received, resulting in the reflected radiation returning to the transceiver from which it was transmitted.

Figure 3:
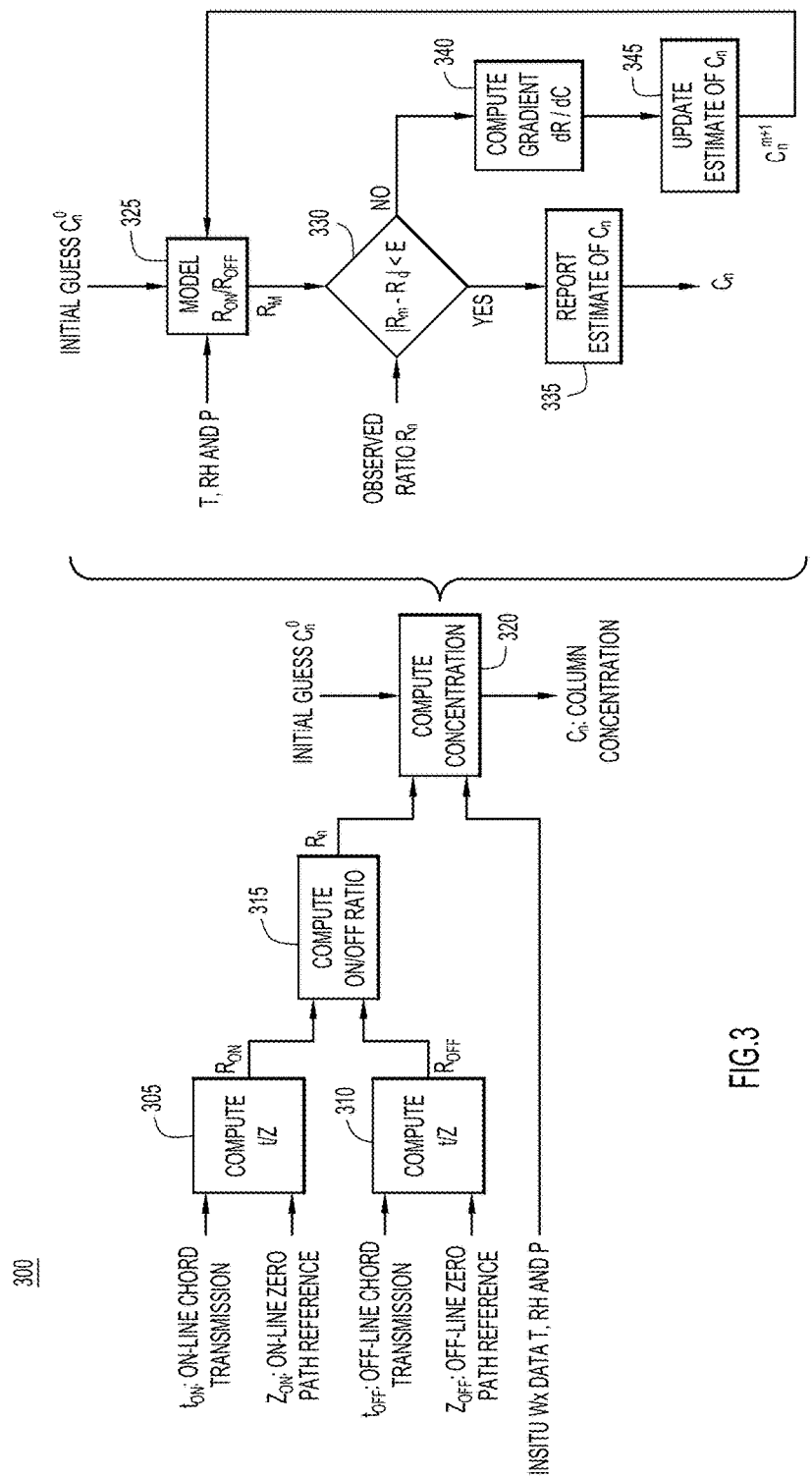
FIG. 3 is a process flow for a process calculating measurement path concentrations for use in real-time spatial mapping of atmospheric gas distribution, according to an example embodiment.

With reference now made to FIG. 3, depicted therein is a process flow 300 illustrating a process for generating an average column or chord concentration over a chord or path between a transmitter and one of the reflectors, such as chords 220*a-z* and/or chords 225*a-z* of FIG. 2. Specifically, illustrated in FIG. 3 is a process by which an average column or chord concentration, in units of dry air mixing ratio (e.g., in parts per million (ppm) or parts per billion (ppb)), along any chord or path between a transceiver/reflector pair is computed using an iterative number method. This process flow starts with a user-defined estimate of the average column concentration, nominally the current standard background value (for carbon dioxide, this would be in the range 390-410 ppm). This value, along with the average temperature, water vapor concentration, and atmospheric pressure along the chord, is used in conjunction with a radiative transfer (RT) model to compute an estimate of the ratio of the on- and off-line transmission values. The same model is used to compute the derivative dR/dC, the gradient change in modeled optical depth ratio given a change in estimated average column concentration. Then, the difference between the current estimate, observed ratio, and dR/dC is used in a gradient search framework to compute updated concentration values until the absolute difference between the observed and estimated ratios approaches a user-defined noise threshold. This approach may be used to compute the average column value over chords with path lengths less than 400 m or for those where only a single value for each of temperature, moisture, and pressure is known.

Accordingly, process flow 300 begins in operations 305 and 310, respectively. Operation 305 calculates the ratio $R_{on}$ of the received on-line wavelength intensity measurement $t_{on}$ to a reference value for an on-line measurement through a chord or path that contains none of the absorptive gas $Z_{on}$. The value of $t_{on}$ may be normalized based upon the initial intensity of the on-line signal transmitted by the transceiver making the measurement. Similarly, in operation 310, the ratio $R_{off}$ of the received off-line wavelength intensity measure $t_{off}$ to a reference value for an off-line measurement through a chord or path that contains none of the absorptive gas $Z_{off}$ is calculated. The value of $t_{off}$ may also be normalized based upon the initial intensity of the off-line signal transmitted by the transceiver making the measurement. In operation 315, the ratio between the on-line and off-line measurements for a particular chord or path (i.e., the "nth" chord or path) is calculated as $R_n$. From this ratio $R_n$, the concentration $C_n$ for the chord or column is calculated in operation 320. As noted above, operation 320 is an iterative method that utilizes a user-defined estimate or "initial guess"; real-time weather data $W_x$ that includes temperature (T), moisture (i.e., relative humidity—RH), and pressure (P) values; and an RT model to determine the concentration $C_n$ for the chord or column. Sub-operations for operation 320 are illustrated through operations 325-345.

As illustrated in operation 325, the initial guess $C_n^0$ for the nth chord and the weather data, P, RH, and T, are provided to the radiative transfer model RT. The RT model models the ratio of the on-line received radiation to the off-line received radiation as $R_M$. In other words, a modeled value $R_M$ for $R_{on}/R_{off}$ is calculated from the model based upon the weather data and the initial guess $C^0$. In operation 330, this modeled ratio $R_M$ is compared to the observed value of $R_n$ calculated in operation 315. If the difference between the observed value $R_n$ and the modeled value $R_M$ is less than a predetermined error threshold E (e.g., a user-defined noise threshold), the initial guess a is determined to be the average concentration of the measured gas over the chord or column. If the difference between $R_n$ and $R_M$ exceeds the error threshold E, the RT model is used in operation 340 to calculate the derivative dR/dC, or the gradient change in modeled optical depth ratio given a change in estimated average column concentration. From this derivative, a new concentration estimate or guess $C_n^{m+1}$ is calculated in operation 345. This new estimate $C_n^{m+1}$ takes the place of initial guess $C_n^0$ in operation 325. Operations 325, 330, 340, and 345 then repeat until a value for $R_M$ determined in operation 325 is found whose difference from the observed ratio $R_n$ is less than the error threshold E. When this occurs, the final value of $C_n$ is reported as the average concentration of the measured gas over the chord or column.

The process of FIG. 3 may be repeated for each chord or path for each transceiver and for each gas that has been measured. For example, if process 300 depicted in FIG. 3 is utilized in a system like that illustrated in FIG. 2, the process may be implemented 104 times if measurements are made for both carbon dioxide and methane. Specifically, the process of flowchart 300 will be implemented 26 times for transceiver 205 and each of reflectors 215a-z for carbon dioxide, 26 times for transceiver 205 and each of reflectors 215a-z for methane, 26 times for transceiver 210 and each of reflectors 215a-z for carbon dioxide, and 26 times for transceiver 210 and each of reflectors 215a-z for methane.

Process 300 of FIG. 3 provides accurate concentrations, particularly for shorter chords or paths that may be characterized by a single set of weather readings, i.e., a single set of T, RH, and P values accurately characterize the entire chord. A segment-oriented algorithmic approach may be used to refine estimates of the average column concentration in cases where the path length exceeds some nominal length (e.g., 400 m), and multiple measurements of T, RH, and P exist for geographically distributed points along or near the line of the chord being evaluated. In such cases, the chord is first divided into N equal lengths, where N is selected based on the length of the chord—the longer the chord, the larger the number of segments. Nominally, the number of segments ranges from 1 to 6 for maximum chord length of 5 km. Next, the latitude, longitude, and height above the geoid for the center points of each segment are computed. Then, an average T and RH value for each center point is computed based on a weighted average of all observed values, where the averaging weights are based on the distance between the center point and the location of each observation. The closer the observation location is to the center of the chord, the greater the weight. A similar technique may be used to compute the atmospheric pressure P at the center of each chord. In addition to the use of the same spatially-weighted averaging approach, an additional hypsometric calculation may be used to adjust the atmosphere P as a function of chord segment height above the geoid. Once the estimated atmospheric states and lengths are computed for each segment, these values are used to compute the ratios for each segment and their corresponding derivatives given a single average estimate of total column concentration. The sum of calculated ratios and the average derivative is used in the same fashion as described above with reference to FIG. 3 to minimize the difference between the observed ratio of transmission values and the totaled model value until an optimal column concentration is determined.

As noted above, the techniques and calculations described herein may be utilized for vertical columns or chords where the vertical atmospheric state vector is defined by ancillary measurement techniques and/or model data, e.g., numeric weather prediction (NWP) model fields.

Figure 4:
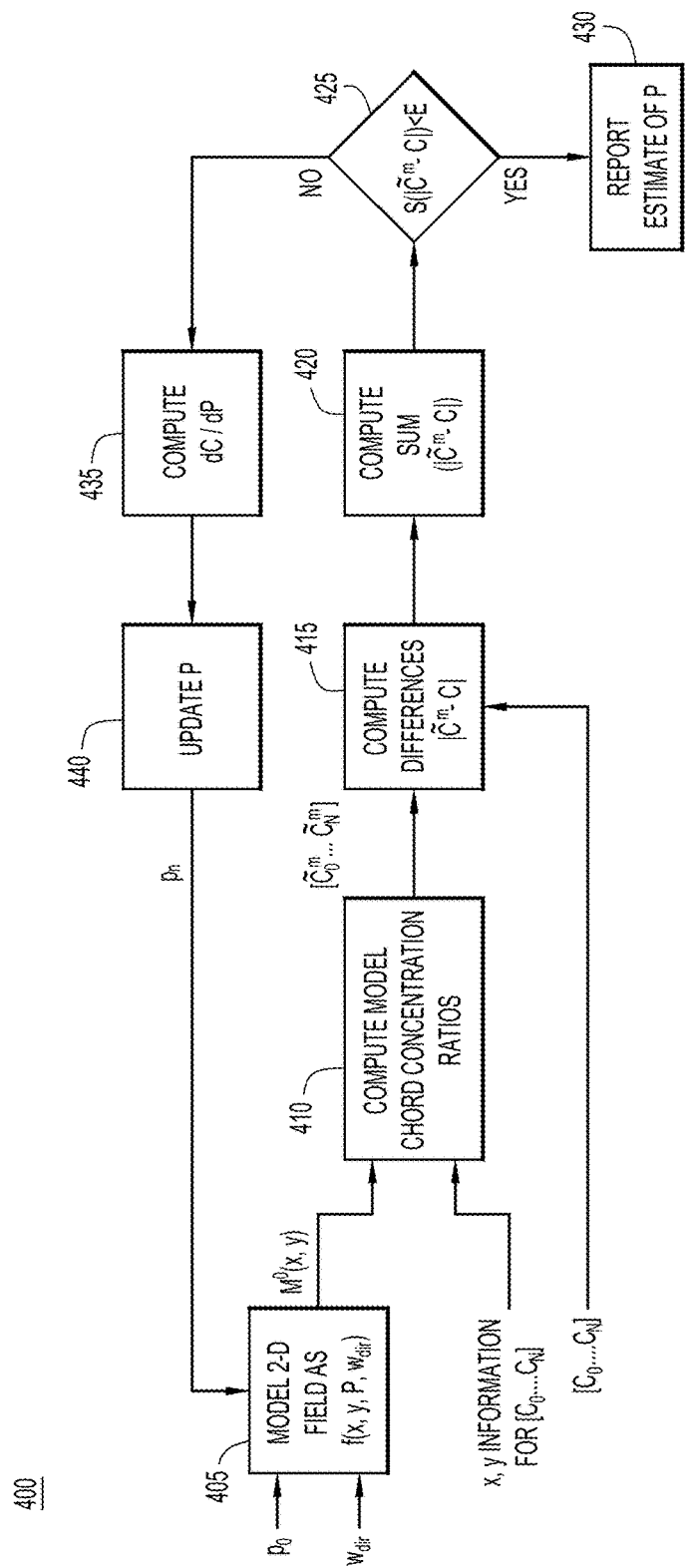
FIG. 4 is a process flow for a process generating real-time spatial maps of atmospheric gas distributions, according to an example embodiment.
Figures 5A, 5B:
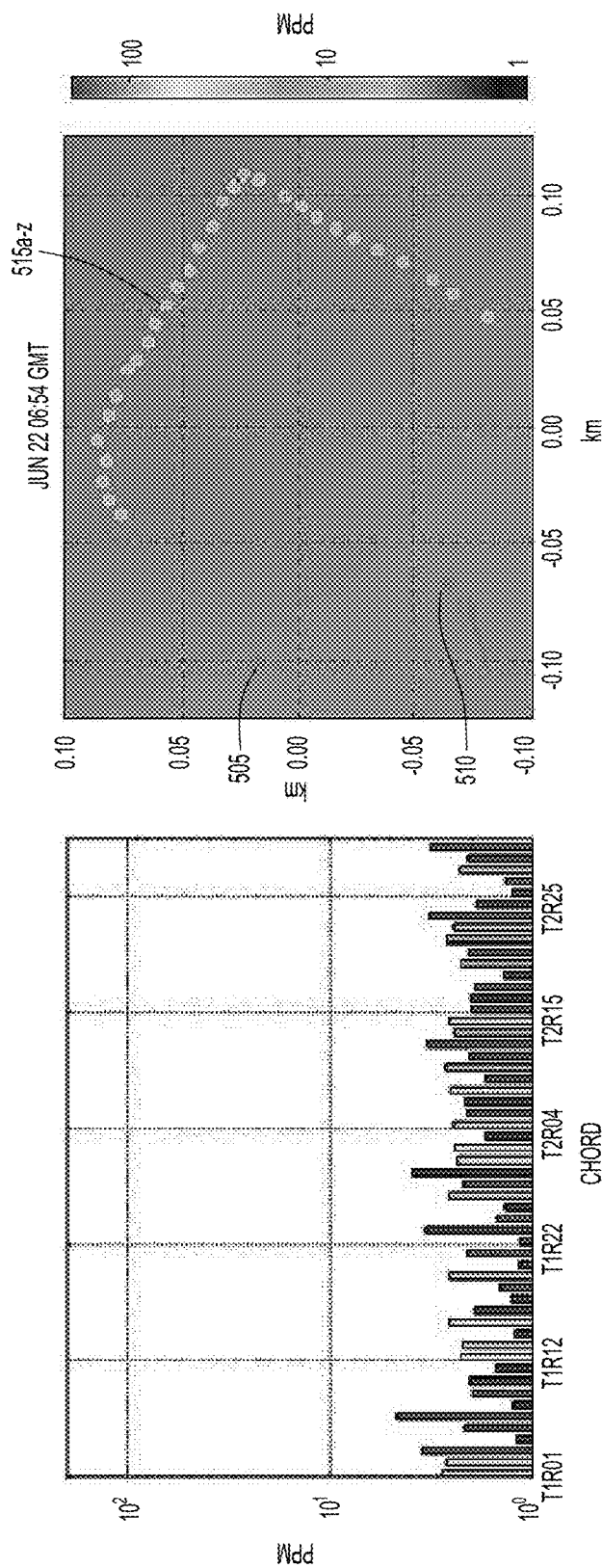
FIG. 5A is a first graph of measurement path concentrations for use in real-time spatial mapping of atmospheric gas distribution, according to an example embodiment.
FIG. 5B is a first real-time spatial map of atmospheric gas distributions generated from the measurement paths graphed in FIG. 5A, according to an example embodiment.
Figures 6A, 6B:
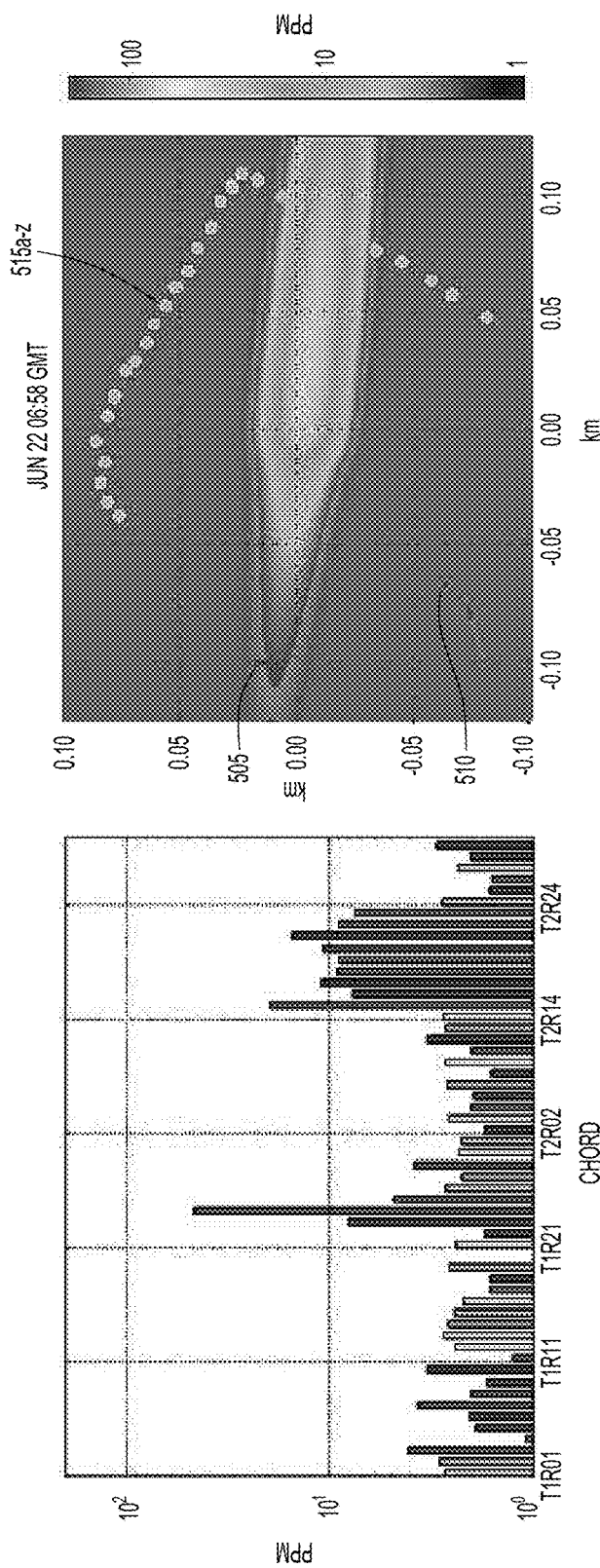
FIG. 6A is a second graph of measurement path concentrations for use in real-time spatial mapping of atmospheric gas distribution, according to an example embodiment.
FIG. 6B is a second real-time spatial map of atmospheric gas distributions generated from the measurement paths graphed in FIG. 6A, according to an example embodiment.
Figures 7A, 7B:
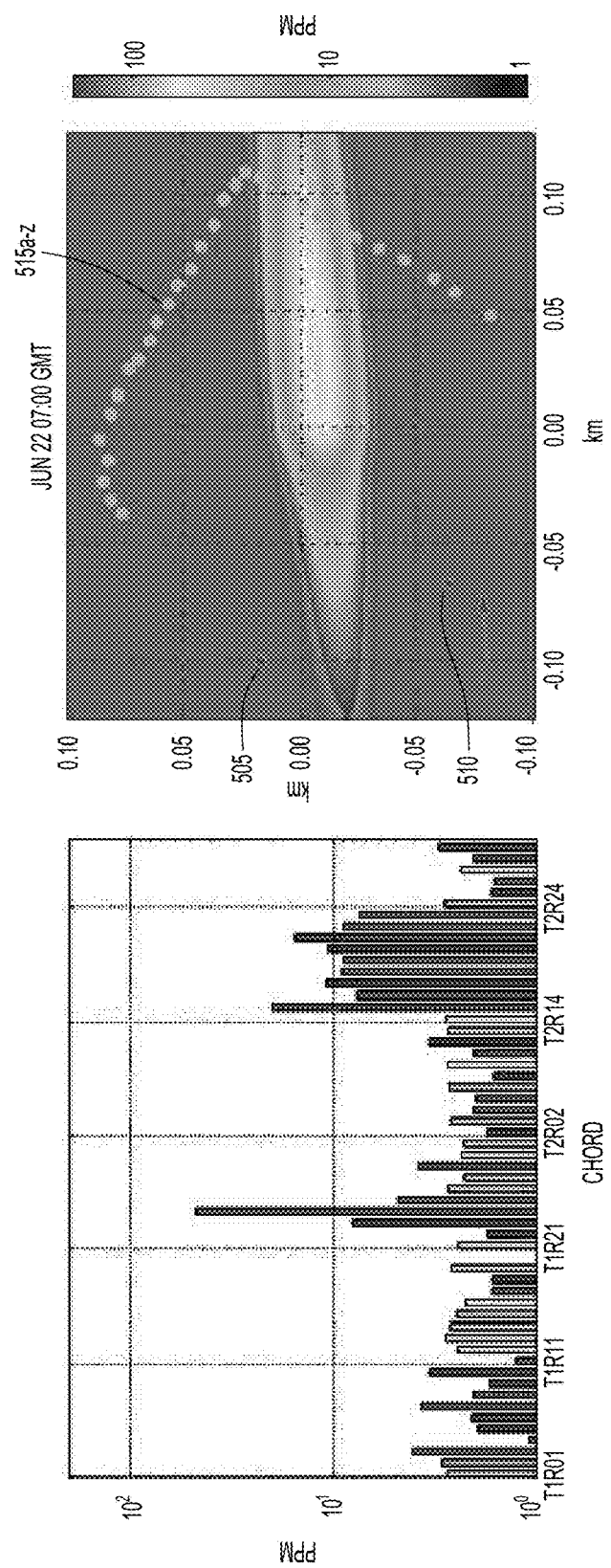
FIG. 7A is a third graph of measurement path concentrations for use in real-time spatial mapping of atmospheric gas distribution, according to an example embodiment.
FIG. 7B is a third real-time spatial map of atmospheric gas distributions generated from the measurement paths graphed in FIG. 7A, according to an example embodiment.
Figure 8B:
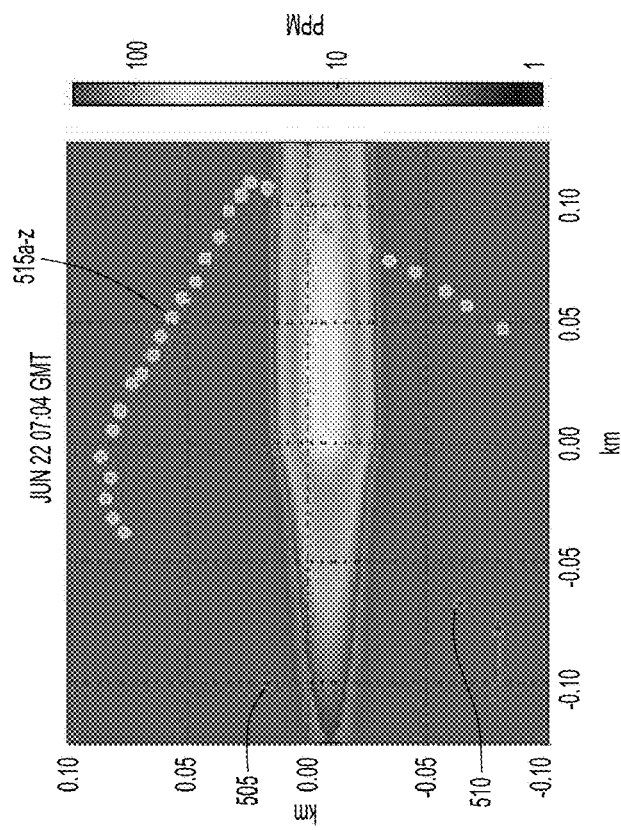
FIG. 8B is a fourth real-time spatial map of atmospheric gas distributions generated from the measurement paths graphed in FIG. 8A, according to an example embodiment.
Figure 8A:
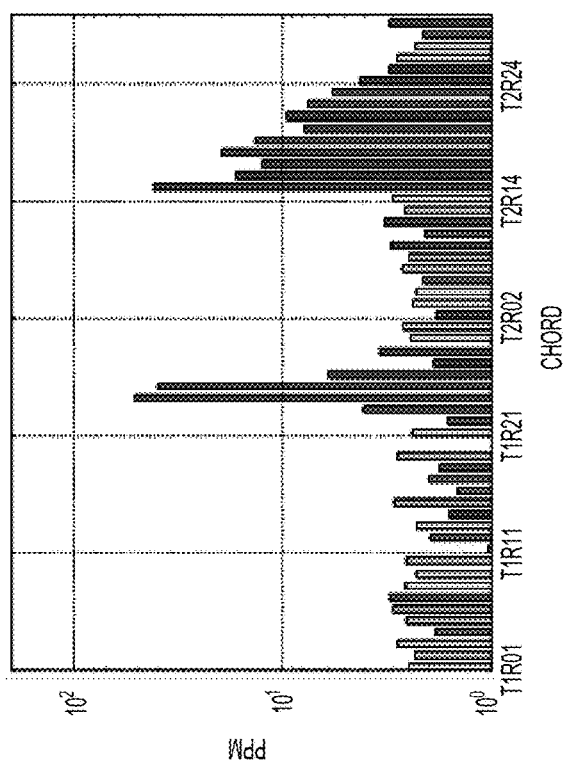
FIG. 8A is a fourth graph of measurement path concentrations for use in real-time spatial mapping of atmospheric gas distribution, according to an example embodiment.
Figures 9A, 9B:
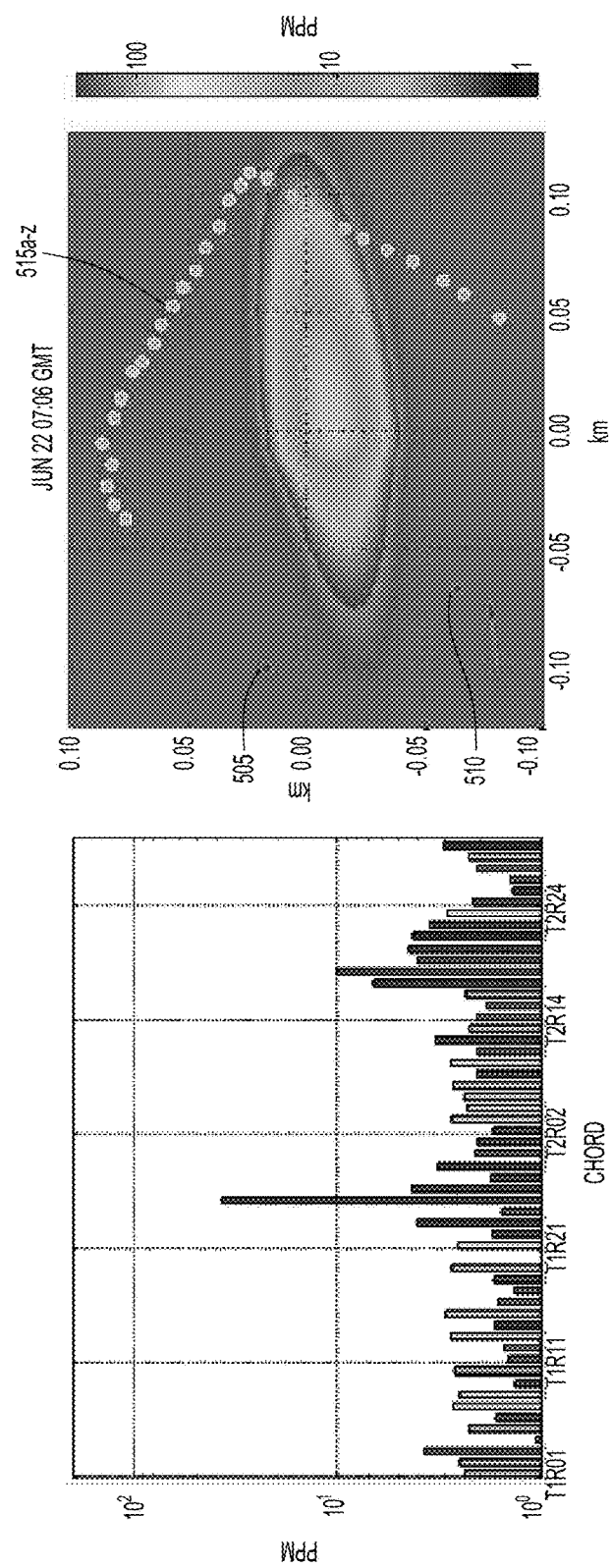
FIG. 9A is a fifth graph of measurement path concentrations for use in real-time spatial mapping of atmospheric gas distribution, according to an example embodiment.
FIG. 9B is a fifth real-time spatial map of atmospheric gas distributions generated from the measurement paths graphed in FIG. 9A, according to an example embodiment.

With reference now made to FIG. 4, depicted therein is a process flow 400 for determining a real-time spatial mapping of atmospheric gas distributions of the present disclosures utilizing the column or chord concentrations calculated according to, for example, process flow 300 of FIG. 3. Process flow 400 begins in operation 405 in which an initial estimate for a concentration map $P^0$ and wind data, such as a vector map of wind direction and magnitude values $w_{dir}$, are used to generate an initial two-dimensional model $M^0$ of the field or area of interest. In operation 410, modeled chord concentrations $C^m$ are determined. In operation 415, differences are determined between respective modeled chord concentrations $[C_0^m \ldots C_N^m]$ and the chord concentrations $[C_0 \ldots C_N]$ determined in, for example, iterations of process flow 300 from FIG. 3. In operation 420, the sum of these differences is computed, and in operation 425 this sum is compared with a predetermined error threshold E. If the sum of the differences is less than the error threshold E, then the initial estimated concentration map $P^0$ is reported as the concentration map for the measurements. If the sum of differences exceeds the error threshold E, then operation 440 calculates the derivative dC/dP, or gradient change in measured concentrations with respect to modeled chord values given a change in model parameters. This derivative is then used to generate a new estimated concentration map $P^{m+1}$ in operation 430. Operations 405, 410, 415, 420, 425, 435, and 440 are then repeated until a concentration map is found in which the differences between the chord concentrations C and the modeled chord concentrations $C^m$ are less than the error threshold value E. When this occurs, the final value of $P_n$ is reported as the concentration map for the measurements.

Illustrated in FIGS. 5A-10A are chord value concentrations with corresponding real-time spatial mapping of atmospheric gas distributions in FIGS. 5B-10B calculated therefrom according to operations like those illustrated in FIGS. 3 and 4. Specifically, chord measurements were taken at intervals of 2 seconds each with a map generated every 2 minutes. The chord measurements illustrated in FIGS. 5A-10A were taken with two transceivers and 30 reflectors, which are illustrated in FIGS. 5B-10B as reference numerals 505, 510, and 515a-z. As illustrated, the techniques described herein accurately measure the gas concentrations over an area of interest with great accuracy and in real-time. Furthermore, as illustrated in FIGS. 5B-10B, the techniques described herein may be utilized to model regions outside an area bounded by the chords between the transmitters 505 and 510 and reflectors 515a-z. Due to the modeling techniques utilized herein, knowing the chord concentrations between transmitters 505 and 510 and reflectors 515a-z, concentrations outside of these chords may also be modeled. While the concentration maps illustrated in FIGS. 5B-10B are for methane, similar maps may be generated for, for example, carbon dioxide utilizing the techniques described herein, as well as for any other gas for which on-line and off-line wavelengths or frequencies are available for use in transceivers like those described herein.

The concentration maps of FIGS. 5B-10B may be particularly relevant for use in detecting gas leaks, detecting where a particular leak is located, and providing a measurement of background concentrations from gas not a result of a leak. For example, the concentration maps illustrated in FIGS. 5B-10B may be used to determine which chords illustrate absorption due to a gas leak. If only background concentration maps are desired (i.e., spatial concentration maps showing the concentration not caused by the leak) the chords identified as experiencing the leak may be identified via a concentration map. The identities of the chords that contain absorption due to the leak may then be provided to, for example, the processing of FIG. 3. The processing of FIG. 3 may be carried out on all chords except the ones identified as experiencing the leak. The result of such processing may be the background concentration not affected by the leak.

With reference now made to FIGS. 11A-F, depicted therein are real-time flux maps that may be generated according to the techniques described herein. Specifically, due to the real-time nature of the spatial concentration maps generated according to the techniques described herein, real-time flux maps may also be generated. For example, by using the values from multiple measurements, differences between these measurements may be utilized to determine how the gas concentrations change over time, i.e., the flux of the concentrations, over the area of interest. FIGS. 11A-F represent such flux maps. According to the examples of FIGS. 11A-11F, the flux maps may be generated by mapping the differences between any two of concentration maps 5B-10B and incorporating this delta concentration map into a multi-box, mass balance calculation to determine a mass flux map of the measured gas (mass per unit area per unit time). The mass flux maps of FIGS. 11A-F may be particularly relevant for use in locating and quantifying sources and/or sinks of the measured gas to include gas leaks from the ground or near-surface equipment.

Figure 12:
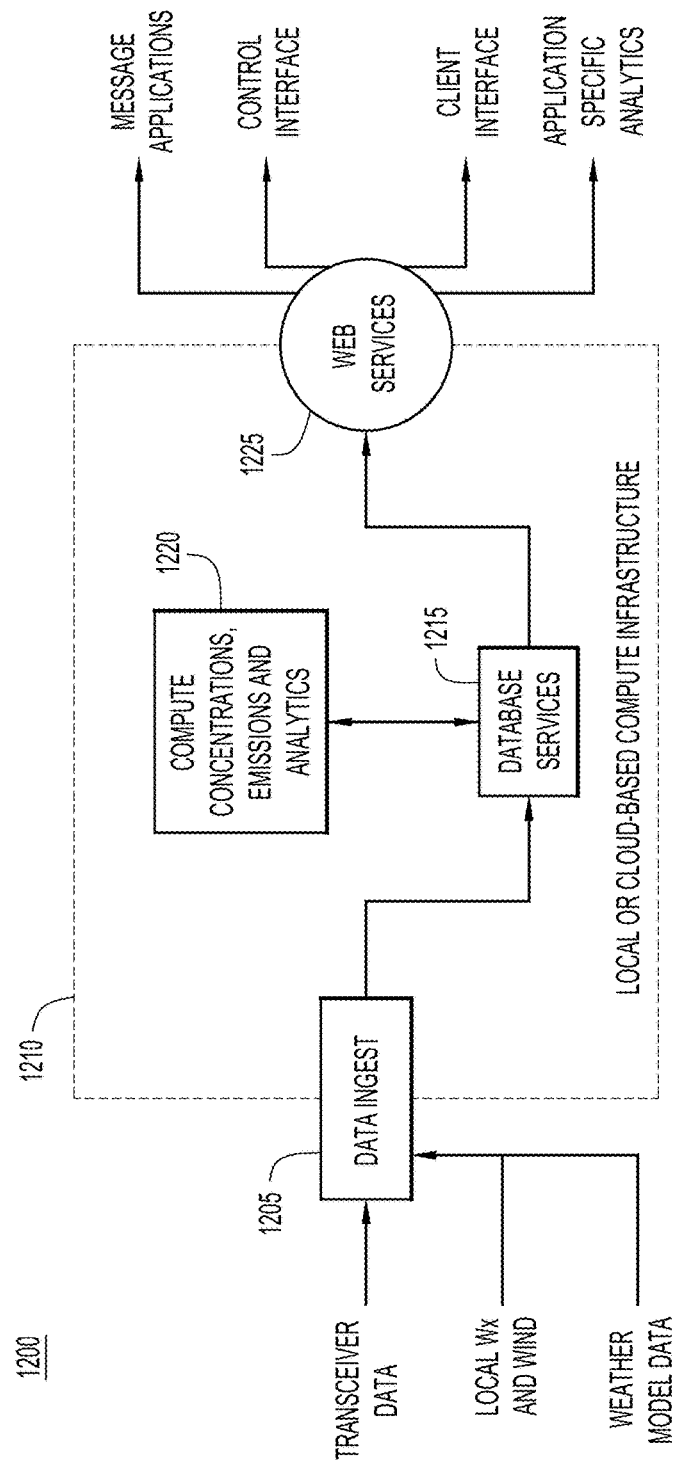
FIG. 12 is a block diagram of a computing environment configured to provide real-time spatial mapping of atmospheric gas distribution, according to an example embodiment.

With reference now made to FIG. 12, depicted therein is an environment diagram 1200 configured to implement the techniques described herein and, in particular, to provide for an end-to-end system that provides for real-time and continuous generation of spatial concentration maps and spatial flux maps of the measured gas. As illustrated, data ingest module 1205 is utilized to input data into the environment 1200. Data ingest module 1205 is configured to receive transceiver data, such as the data acquired from a transceiver 100 as illustrated in FIG. 1, as well as local weather and wind data, and data from weather models. Accordingly, data ingest module 1205 is configured to receive the inputs that may be utilized in process flow 300 of FIG. 3.

Data ingest module 1205 may be embodied as a portion of a processing and communication module local to one or more of the transceivers that acquire the transceiver data, such as processing and communication module 110 of FIG. 1. For example, a processing and communication module associated with an arrangement like that illustrated in FIGS. 2, 13, 14A, and/or 14B may be configured to provide the processing illustrated in one or more of FIGS. 3 and/or 4. Accordingly, data ingest module 1205 may be configured to access a wired or wireless interface of the processing and communication module to receive data from one or more transceivers. Taking the arrangement of FIG. 2 as an example, transceiver 205 may be configured to receive data from a local transceiver via a communication link, like communication link 102 of FIG. 1, and receive transceiver data from transceiver 210 via wired or wireless communications initiated from a processing and communication module associated with transceiver 210. The processing and communication module would then be configured to carry out the processing illustrated in FIGS. 3 and/or 4 for all of the transceivers.

According to other example embodiments, data ingest module 1205 may be configured as a gateway to a cloud-based computing environment. Accordingly, each of the processing and communication modules associated with a transceiver will provide its data to the cloud-based data ingest module via a wired or wireless link.

The data received from data ingest module 1205 are utilized by compute infrastructure 1210. According to the example embodiment of FIG. 12, compute infrastructure 1210 stores and processes the received data via processing like that illustrated in FIGS. 3 and/or 4. To facilitate this processing, compute infrastructure 1210 includes data storage services 1215 and processing services 1220. Data storage services 1215 may include both hardware and software components. For example, data storage services 1215 may include memory or storage devices, including magnetic hard disks, solid state drives, and/or removable media drives (e.g., floppy disk drive, optical disc drives, removable magneto-optical drives, and optical storage drives). These hardware components may physically store the data received from the transceivers via data ingest module 1205. Data storage services 1215 may also include software components, such as a database management system, to allow easy organization and access to the data stored in the physical storage devices.

Processing services 1220 may also include hardware and software components. For example, hardware components may include one or more processors configured to execute a series of instructions to carry out the processes illustrated in FIGS. 3 and/or 4. The processors may be embodied as an individual processor, or a plurality of processors in a multi-processing arrangement may also be employed to execute the sequences of instructions. The hardware components of processing services 1220 may also include special purpose logic devices (e.g., application-specific integrated circuits (ASICs)) or configurable logic devices (e.g., simple programmable logic devices (SPLDs), complex programmable logic devices (CPLDs), and field programmable gate arrays (FPGAs)), that, in addition to microprocessors and digital signal processors, are types of processing circuitry. The processing circuitry may be located in one device or distributed across multiple devices.

The software components contained in processing services 1220 may include one or more sequences of one or more instructions contained in a memory, such as the memory contained in data storage services 1215. The instructions include instructions that cause the hardware components of processing services 1220 to carry out processing as illustrated in FIGS. 3 and/or 4. The instructions may also cause the hardware components of processing services 1220 to carry out additional operations, including instructions to carry out reporting and presentation operations on the data received from the transceivers, the spatial concentration maps, and the spatial flux maps generated by processing services 1220. As previously noted above, the processing services may be located in a device local to one or more of the transceivers, be located in a cloud or server-based system remote from the transceivers, or be distributed across local and remote devices. Also illustrated in environment diagram 1200 are web services 1225. Web services 1225 are used to communicate the results of processing services 1220 to users and to receive instructions that will be communicated back to processing services 1220 and the transceivers that provide the data through data ingest module 1205.

For example, web services 1225 may leverage electronic message services such as electronic mail (e-mail), instant messaging protocol applications, and short message service (SMS) applications to communicate the results of processing services 1220 to users. Similarly, application programming interfaces (APIs) may be utilized by web services 1225 to access and communicate the results of processing services 1220 to users. Web services 1225 may provide a user interface and/or a control interface that permit users to access real-time spatial mappings of atmospheric gas distributions and real-time spatial flux mappings of the measured gas. The user and control interfaces may also enable users to select from predetermined groups of measurement arrangements. For example, a particular user group may have established a plurality of arrangements of transceivers and reflectors. Web services 1225 may provide interfaces that permit users to select from this plurality of arrangements to receive the raw transceiver data or the results of the processing as illustrated in FIGS. 3 and/or 4.

Web services 1225 may also include control interfaces that allow users to control, monitor, or troubleshoot one or more transceivers in a measurement arrangement. For example, through web services 1225, users may be enabled to execute measurement operations, reposition transceivers, or request diagnostic information from one or more transceivers and/or processing and communication modules. When such control operations are enabled, data ingest 1205 may be configured as a two-way gateway that allows compute infrastructure 1220 to communicate with one or more transceivers and/or processing and communication modules via the same channels through which data ingest 1205 receives the data from the one or more transceivers and/or processing and communication modules.

Figure 13:
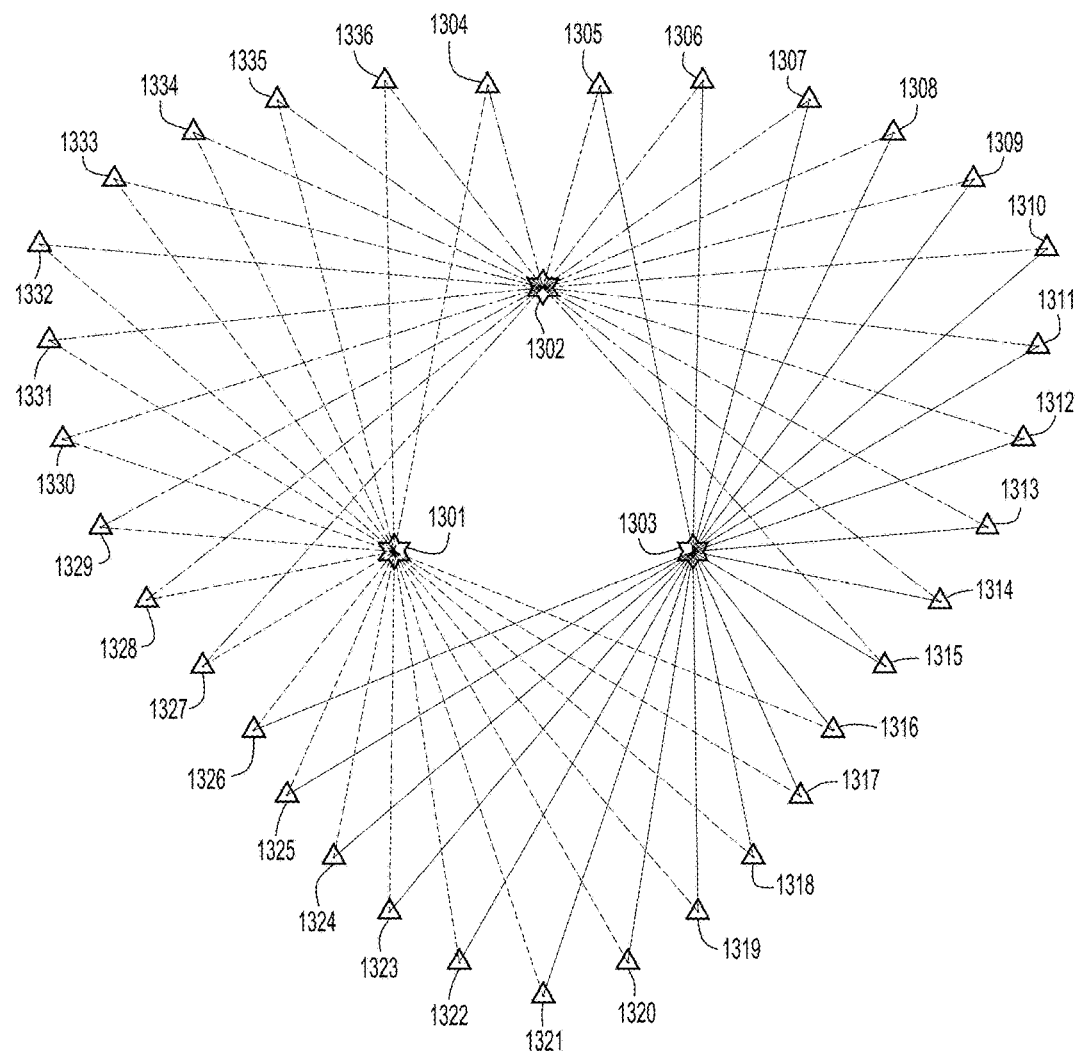
FIG. 13 is a second arrangement of transceivers and reflectors configured to provide real-time spatial mapping of atmospheric gas distribution, according to an example embodiment.

With reference now made to FIG. 13, depicted therein is an alternative arrangement of transceivers 1301, 1302, and 1303 and reflectors 1304-1336 that may be leverage to carry out the measurement techniques of the present disclosure. The arrangement of FIG. 13 places reflectors 1304-1336 in three intercepting parabolic shapes, with transceivers 1301-1303 arranged within the parabolic arrangement of reflectors. Through the use of such a parabolic arrangement and the use of three transceivers 1301-1303, the number of chords or measurement paths for a particular area may be increased or maximized. By increasing or maximizing the number of chords for a particular area, the resolution and/or accuracy of the calculated concentration maps may be increased. For example, compared with an arrangement of transceivers and reflectors like those illustrated in FIGS. 14A and 14B, described in more detail below, the arrangement of FIG. 13 may cover a similar sized area of interested, but does so with a higher number of chords. This higher number of chords in a similar area of interest may result in more accurate gas concentration maps generated via the processing illustrated in FIGS. 3 and 4.

Figure 14A:
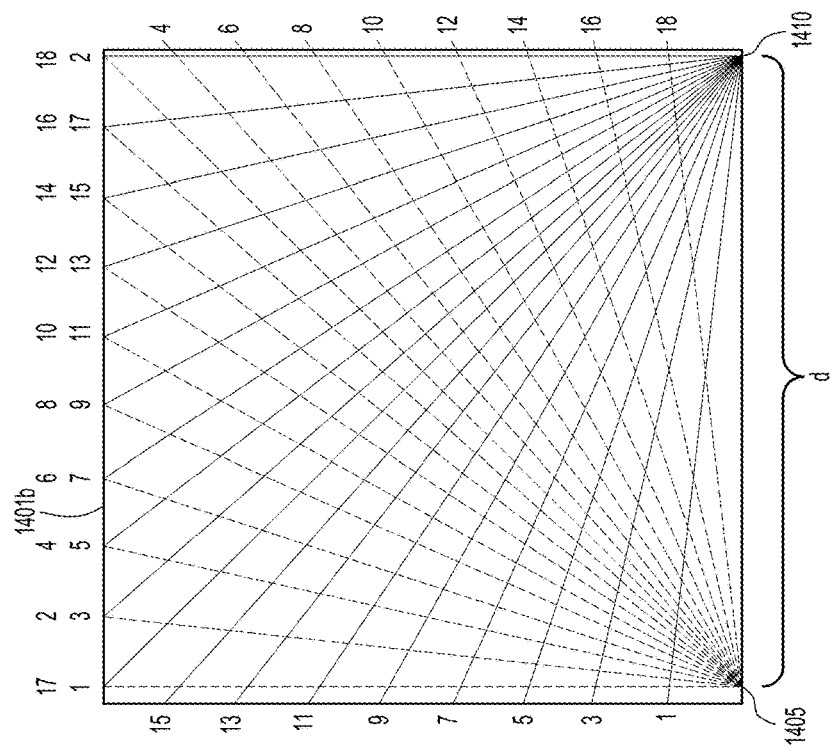
FIG. 14A is a third arrangement of transceivers and reflectors configured to provide real-time spatial mapping of atmospheric gas distribution, according to an example embodiment.
Figure 14B:
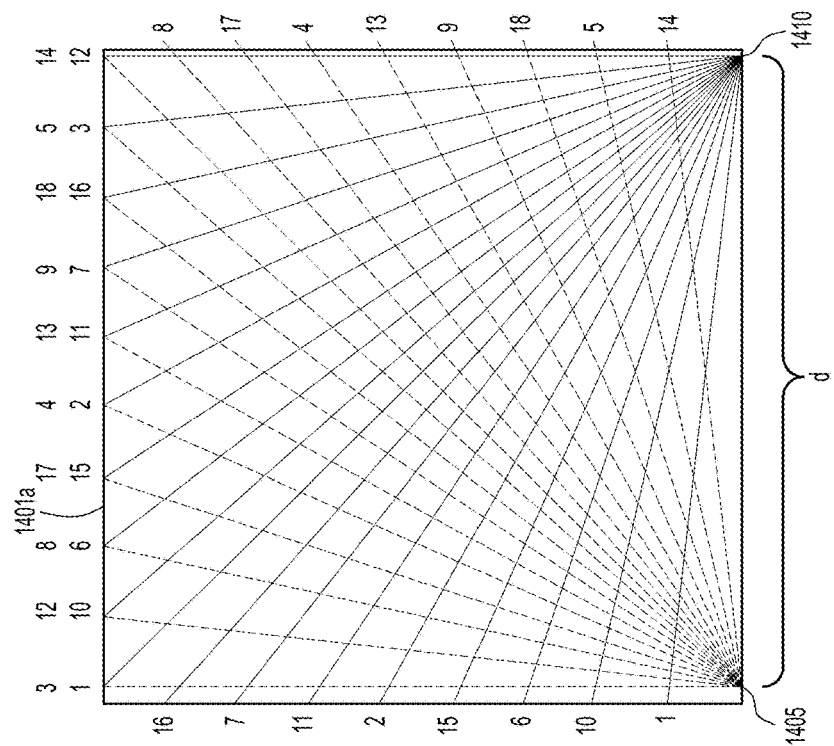
FIG. 14B is a fourth arrangement of transceivers and reflectors configured to provide real-time spatial mapping of atmospheric gas distribution, according to an example embodiment.

With reference now made to FIGS. 14A and 14B, depicted therein are arrangements of transceivers 1405 and 1410 and reflectors arranged in a box shape. The reflectors of FIGS. 14A and 14B are indicated by reference numerals that correspond to the order in which each of transceivers 1405 and 1410 take measurements from the reflectors. The arrangement of FIGS. 14A and 14B illustrates a sequence of measurements by the transceivers 1405 and 1410 that may result in measurements that cover the entire area of interest in a way that minimizes the amount of time an area of interest may go unmeasured. For example, when used in natural gas extraction applications, increased concentrations of natural gas will want to be discovered quickly due to the combustible, and therefore, dangerous nature of the gas. Accordingly, in such applications, an arrangement of transceivers and reflectors as illustrated in FIGS. 14A and 14B may be desirable as such arrangements ensure that no portions of areas of interest 1401a and 1401b go unmeasured for a significant period of time. As a possible added benefit, arrangements like those illustrated in FIGS. 14A and 14B may serve to maximize the orthogonality of the chords being measured. This increase in orthogonality, accomplished by maximizing the distance "d" between the transceivers over the areas of interest 1401a and 1401b, may result in an increased accuracy for certain applications.

With reference now made to FIG. 15, depicted therein is process flow 1500 configured to calibrate one or more transceivers using a calibration target. Process flow 1500 begins in operation 1505 where a calibration target is arranged such that the transmitted radiation from a transceiver can be directed at it. For example, a reflector may be positioned in close proximity to the transceiver to generate a short-path atmospheric return with negligible absorption. A gas cell containing a known gas or mixture of gases may be arranged between the transceiver and the reflector to provide a known absorption. For purposes of process flow 1500, the transceiver being calibrated requires different gain settings for the receiver signal chain to accommodate varying intensities in the collected radiation from chord to chord. These different gain settings require unique calibration parameters for each. In operation 1505, the transceiver is directed at the calibration target. In operation 1510, the receive channel gain value is set to the first value from the set of values for which calibration is required. In operation 1515, the transceiver or the calibration target is "dithered" or moved continuously (e.g., up and down, left and right, circularly, elliptically, randomly, etc.) within a small angular range. This dithering technique may reduce the effects of speckle and increase the SNR of the measurement. In operation 1520, data is gathered during the dithering of the transceiver over a predetermined dwell period that is sufficiently long to result in a measurement with high SNR. The optical depth ratio of the short-path calibration chord is then used in operation 1525 along with the current calibration coefficient to compute the new calibration coefficient for the current receiver gain setting. In operation 1530, the new calibration coefficient is saved and applied within the processing and communication module as depicted in FIG. 1. If the transceiver is configured to use more than one receiver gain setting, the process flow 1500 moves to operation 1545, where the gain setting is changed to the next value in the list of gain values for which calibration is required. The calibration process depicted by operations 1520-1535 is performed for each gain value before the process proceeds to operation 1540, in which the transceiver dithering is stopped and standard measurement operation is resumed. The calibration process depicted in process flow 1500 may be performed for each gas (i.e., for each pair or set of on-line and off-line wavelengths) for which the transceiver is configured to measure.

The above description is intended by way of example only. Although the techniques are illustrated and described herein as embodied in one or more specific examples, it is nevertheless not intended to be limited to the details shown, since various modifications and structural changes may be made within the scope and range of equivalents of the claims.

What is claimed is:

1. An apparatus comprising:
 a plurality of reflectors arranged over an area;
 one or more transceivers configured to transmit radiation at each of the plurality of reflectors at a plurality of wavelengths, receive radiation reflected from each of the plurality of reflectors at the plurality of wavelengths, and generate signals indicative of intensities of the radiation received at the plurality of wavelengths; and
 a processor, wherein the processor is configured to:
  receive, at a first time, first signals from the one or more transceivers indicative of intensities of the radiation received at the plurality of wavelengths;
  receive, at a second time, second signals from the one or more transceivers indicative of intensities of the radiation received at the plurality of wavelengths;
  calculate a first concentration of a gas within the area based upon the first signals;
  calculate a second concentration of the gas within the area based upon the second signals; and
  calculate a change in concentration of the gas within the area between the first time and the second time.

2. The apparatus of claim 1, wherein each of the one or more transceivers comprises an intensity- or frequency-modulated, continuous-wave laser absorption spectrometer.

3. The apparatus of claim 2, wherein a first transceiver of the one or more transceivers is configured to simultaneously transmit the radiation at a first wavelength and a second wavelength.

4. The apparatus of claim 1, wherein each of the plurality of reflectors comprises a retroreflector.

5. The apparatus of claim 1, wherein radiation at a first wavelength of the plurality of wavelengths is absorbed by the gas to a lesser extent than radiation at a second wavelength of the plurality of wavelengths.

6. The apparatus of claim 1, wherein the one or more transceivers comprises at least two transceivers, wherein a first of the at least two transceivers is configured to transmit radiation at a first wavelength and a second wavelength, and wherein a second of the at least two transceivers is configured to transmit radiation at a third wavelength and a fourth wavelength.

7. The apparatus of claim 6, wherein the first wavelength is different than each of the third wavelength and the fourth wavelength.

8. The apparatus of claim 6, wherein the first wavelength is the same as the third wavelength and the second wavelength is the same as the fourth wavelength.

9. The apparatus of claim 1, further comprising generating a flux map of the area based upon the change in concentration of the gas.

10. A method comprising:
 arranging a plurality of reflectors throughout an area;
 transmitting, at a first time from one or more transceivers, radiation of a first plurality of wavelengths at each of the plurality of reflectors;
 receiving, at the one or more transceivers, radiation of the first plurality of wavelengths reflected from each of the plurality of reflectors;
 transmitting, at a second time from the one or more transceivers, radiation of a second plurality of wavelengths at each of the plurality of reflectors;
 receiving, at the one or more transceivers, radiation of the second plurality of wavelengths reflected from each of the plurality of reflectors;
 transmitting, to one or more processors, first signals comprising data indicative of intensities of the radiation of the first plurality of wavelengths reflected from each of the plurality of reflectors;
 transmitting, to the one or more processors, second signals comprising data indicative of intensities of the radiation of the second plurality of wavelengths reflected from each of the plurality of reflectors;
 calculating, via the one or more processors, a first concentration of a gas within the area based upon the first signals;
 calculating, via the one or more processors, a second concentration of the gas within the area based upon the second signals received; and
 calculating, via the one or more processors, a change in concentration of the gas within the area between the first time and the second time.

11. The method of claim 10, wherein the first plurality of wavelengths comprises a first wavelength and a second wavelength, and the second plurality of wavelengths comprises a third wavelength and a fourth wavelength.

12. The method of claim 11, wherein the first wavelength is absorbed by the gas to a lesser extent than the second wavelength.

13. The method of claim 11, wherein the first wavelength is the same as the third wavelength, and the second wavelength is the same as the fourth wavelength.

14. The method of claim 11, wherein the first wavelength is different than each of the third wavelength and the fourth wavelength.

15. The method of claim 10, further comprising calibrating the one or more transceivers, wherein the calibrating comprises directing the one or more transceivers at a calibration target and dithering the calibration target or the one or more transceivers while transmitting radiation towards the calibration target.

16. A method comprising:
arranging a plurality of reflectors throughout an area;
transmitting, from one or more transceivers, radiation of a first plurality of wavelengths at each of the plurality of reflectors;
receiving, at the one or more transceivers, radiation of the first plurality of wavelengths reflected from each of the plurality of reflectors;
transmitting, from the one or more transceivers, radiation of a second plurality of wavelengths at each of the plurality of reflectors;
receiving, at the one or more transceivers, radiation of the second plurality of wavelengths reflected from each of the plurality of reflectors;
transmitting, to one or more processors, first signals comprising data indicative of intensities of the radiation of the first plurality of wavelengths reflected from each of the plurality of reflectors;
transmitting, to the one or more processors, second signals comprising data indicative of intensities of the radiation of the second plurality of wavelengths reflected from each of the plurality of reflectors;
calculating, via the one or more processors, a concentration of a first gas within the area based upon the first signals; and
calculating, via the one or more processors, a concentration of a second gas within the area based upon the second signals received.

17. The method of claim 16, wherein the first gas comprises carbon dioxide and the second gas comprises methane.

18. The method of claim 16, wherein the first plurality of wavelengths and the second plurality of wavelengths are concurrently transmitted from the one or more transceivers.

19. The method of claim 16, wherein the one or more transceivers comprises at least two transceivers, wherein a first of the at least two transceivers is configured to transmit a first wavelength and a second wavelength of the first plurality of wavelengths, and a second of the at least two transceivers is configured to transmit a third wavelength and a fourth wavelength of the first plurality of wavelengths, and wherein the first of the plurality of wavelengths is different than each of the third wavelength and the fourth wavelength.

20. The method of claim 16, further comprising calibrating the one or more transceivers, wherein the calibrating comprises directing the one or more transceivers at a calibration target and dithering the calibration target or the one or more transceivers while transmitting radiation towards the calibration target.

* * * * *